(12) United States Patent
Toshikiyo et al.

(10) Patent No.: US 10,386,295 B2
(45) Date of Patent: Aug. 20, 2019

(54) VEGETATION INDEX CALCULATION METHOD AND VEGETATION INDEX CALCULATION DEVICE

(71) Applicant: Panasonic Intellectual Property Management Co., Ltd., Osaka (JP)

(72) Inventors: Kimiaki Toshikiyo, Osaka (JP); Bing Xue, San Jose, CA (US)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/744,955

(22) PCT Filed: Jul. 19, 2016

(86) PCT No.: PCT/JP2016/003385
§ 371 (c)(1),
(2) Date: Jan. 15, 2018

(87) PCT Pub. No.: WO2017/017929
PCT Pub. Date: Feb. 2, 2017

(65) Prior Publication Data
US 2018/0209898 A1    Jul. 26, 2018

Related U.S. Application Data

(60) Provisional application No. 62/197,852, filed on Jul. 28, 2015.

(51) Int. Cl.
*G01N 21/25* (2006.01)
*G01N 21/27* (2006.01)
(Continued)

(52) U.S. Cl.
CPC ......... *G01N 21/255* (2013.01); *G01N 21/274* (2013.01); *G01N 21/31* (2013.01);
(Continued)

(58) Field of Classification Search
CPC ............ G01J 1/4204; G01J 2003/2826; G01N 2021/1797; G01N 21/274
See application file for complete search history.

(56) References Cited

U.S. PATENT DOCUMENTS 5,980,052 A * 11/1999 Thor ................. F21S 11/00
359/877
8,558,884 B2   10/2013 Ingram, Jr. et al.
(Continued)

FOREIGN PATENT DOCUMENTS

JP    2004-301810    10/2004
JP    2006-101768     4/2006
(Continued)

OTHER PUBLICATIONS

Yu Sun "Use of ambient light in remote photoplethysmographic systems: comparison between a high-performance camera and a low-cost webcam", Mar. 2012, Journal of Biomedical Optics (Year: 2012).*

(Continued)

*Primary Examiner* — Maurice C Smith
(74) *Attorney, Agent, or Firm* — McDermott Will & Emery LLP

(57) ABSTRACT

A vegetation index calculation method is a method for calculating a vegetation index indicating a vegetation state in an earth's surface using an imaging unit and a flight vehicle, and the vegetation index calculation method includes an illumination spectrum acquisition step of acquiring a spectrum of illumination light with which the earth's surface is irradiated and a reflection spectrum acquisition step of acquiring a reflection spectrum of the earth's surface by the illumination light. The vegetation index calculation method also includes a calibration step of calibrating the reflection spectrum using the illumination spectrum and a step of calculating the vegetation index of the earth's surface based on a calibrated spectrum obtained through the calibration step.

11 Claims, 10 Drawing Sheets

(51) Int. Cl.
*G01N 21/55* (2014.01)
*G01N 33/00* (2006.01)
*G01N 21/31* (2006.01)
*G01N 21/17* (2006.01)
*G01N 21/84* (2006.01)

(52) U.S. Cl.
CPC ......... *G01N 21/55* (2013.01); *G01N 33/0098* (2013.01); *G01N 2021/1797* (2013.01); *G01N 2021/8466* (2013.01); *G01N 2201/0636* (2013.01)

(56) References Cited

U.S. PATENT DOCUMENTS

| | | | | |
|---|---|---|---|---|
| 2001/0016053 A1* | 8/2001 | Dickson | ............... | G01J 3/2803 382/110 |
| 2005/0151965 A1* | 7/2005 | Bissett, III | ............... | G01J 3/28 356/328 |
| 2014/0022381 A1* | 1/2014 | Heinold | ............... | G01N 21/27 348/135 |
| 2016/0055687 A1* | 2/2016 | Blank, Sr. | ............... | G07C 5/085 701/4 |
| 2016/0069741 A1* | 3/2016 | Ritter | ............... | G01J 3/0297 356/402 |

FOREIGN PATENT DOCUMENTS

| | | |
|---|---|---|
| JP | 2006-314215 | 11/2006 |
| JP | 2010-256303 | 11/2010 |

OTHER PUBLICATIONS

International Search Report of PCT application No. PCT/JP2016/003385 dated Oct. 18, 2016.

\* cited by examiner

NDVI and detection object

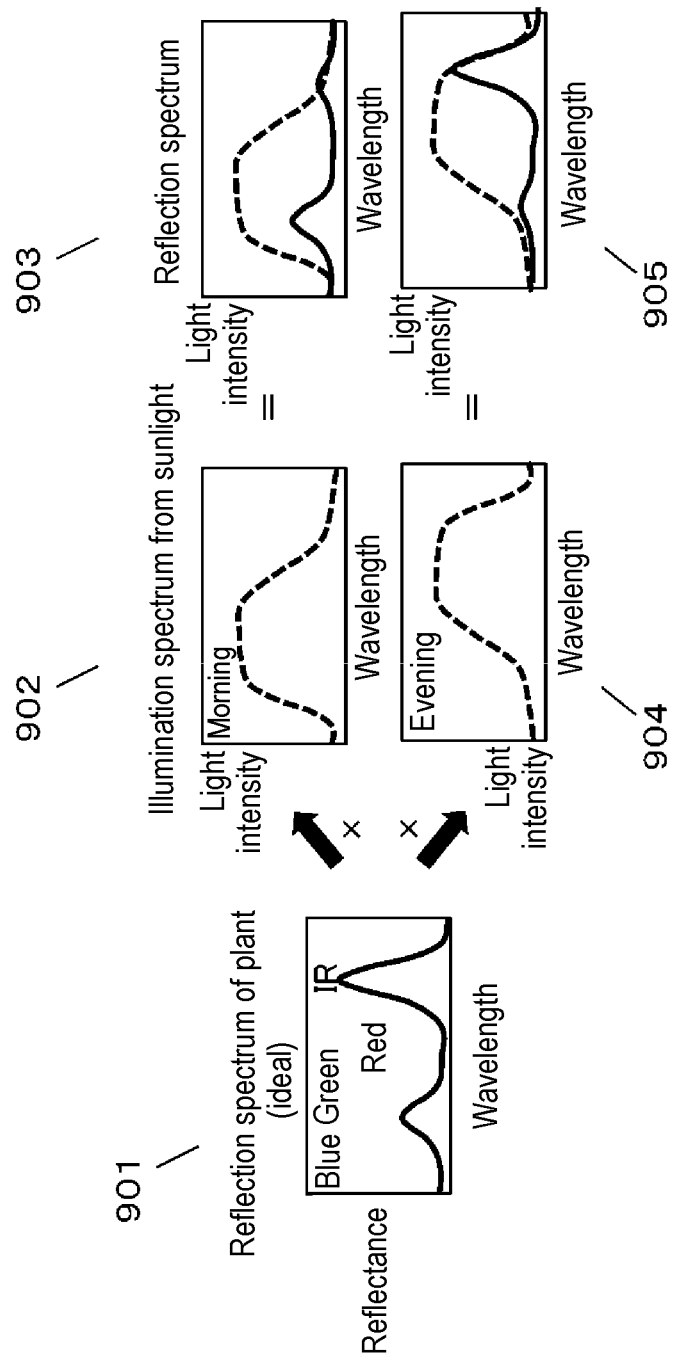

VEGETATION INDEX CALCULATION METHOD AND VEGETATION INDEX CALCULATION DEVICE

This application is a U.S. national stage application of the PCT International Application No. PCT/JP2016/003385 filed on Jul. 19, 2016, which claims the benefit of U.S. Provisional Application 62/197,852 filed on Jul. 28, 2015, the contents all of which are incorporated herein by reference.

FIELD OF THE INVENTION

The present disclosure relates to a vegetation index calculation method and a vegetation index calculation device, for indexing a vegetation state of a farmland in order to mainly evaluate a distribution situation or a growth condition of a crop.

DESCRIPTION OF THE RELATED ART

FIG. 8 is a diagram illustrating a conventional vegetation index calculation method and a conventional vegetation index calculation device. In FIG. 8, image sensor 800 mounted on a flight vehicle captures an image of target area 803 in earth's surface 802 irradiated by light source 801. Image sensor 800 can capture a multi-spectral image or a hyper-spectral image. Generally, plants absorb wavelengths in blue and red regions, and strongly reflect a wavelength in a near-infrared region using chlorophyll included in a chloroplast. Therefore, the vegetation state of the earth's surface can be analyzed using a spectrum of reflected light from the earth's surface. The image captured by image sensor 800 is stored in memory 805 through input and output 809 of computer 804. In the image of the earth's surface captured from the sky by the flight vehicle, the spectrum of the earth's surface cannot accurately be obtained because aerosol in the air scatters or absorbs illumination light or reflected light from the light source. For this reason, calibration is performed using calibration database 806 previously prepared in each type of the earth's surface or calibration database 807 previously prepared in each aerosol type. The calibration is performed by a program stored in program memory 808, processor 810, and memory 811, the captured image stored in memory 805 is calibrated using calibration databases 806, 807, and a spectrum analysis is performed on the calibrated image, thereby calculating a vegetation index.

CITATION LIST

Patent Literature

PTL 1: U.S. Pat. No. 8,558,884

SUMMARY OF THE INVENTION

However, not only a reflection spectrum of the earth's surface is affected by the aerosol in the air, but also the reflection spectrum is largely affected by the illumination spectrum from sunlight that is the light source. It is difficult to accurately calculate the vegetation index because the illumination spectrum from the sunlight changes according to a weather condition or a time period.

In order to solve the above problems, the present invention provides a vegetation index calculation method for calculating a vegetation index indicating a vegetation state in an earth's surface using a flight vehicle including an imaging unit. The vegetation index calculation method includes an illumination spectrum acquisition step of acquiring a spectrum of illumination light with which the earth's surface is irradiated, and a reflection spectrum acquisition step of acquiring a reflection spectrum of the earth's surface by the illumination light. The vegetation index calculation method also includes a calibration step of calibrating the reflection spectrum using the illumination spectrum and a step of calculating the vegetation index of the earth's surface based on a calibrated spectrum obtained through the calibration step.

With the vegetation index calculation method, the spectrum in which the influence of the illumination spectrum from the light source is reduced can be obtained, and the vegetation index can be calculated more accurately.

BRIEF DESCRIPTION OF THE DRAWINGS

FIG. 9 is an explanatory view illustrating the influence of the illumination spectrum in the conventional vegetation index calculation method.

DETAILED DESCRIPTION OF THE PREFERRED EMBODIMENTS

Knowledge of the Present Inventors Developing of the Invention According to the Present Disclosure FIG. 9 is a conceptual diagram illustrating an influence of an illumination spectrum from sunlight. Graph 901 is the reflection spectrum of the earth's surface when there is no influence of the illumination spectrum (when the illumination spectrum is flat). Plants in the earth's surface have a small reflectance in a blue region (about 450 nm to about 495 nm) and a red region (about 620 nm to about 750 nm) because the plants absorb wavelengths of the blue and red regions, have a slightly strong reflectance in a green region (about 495 nm to about 570 nm), and have an extremely strong reflectance in a near-infrared region (about 750 nm to about 1000 nm). Graph 902 illustrates the illumination spectrum from sunlight in a time period of morning, and graph 903 illustrates the reflection spectrum of the earth's surface in the time period of morning. As illustrated in graph 902, in the illumination spectrum in the time period of morning, light intensity in the red to near-infrared regions is weakened in the time period of morning. Therefore, as illustrated in graph 903, the reflection spectrum has the light intensity smaller than it really is in the red region to an infrared (IR) region. On the other hand, graph 904 illustrates a sunlight spectrum in a time period of evening, and graph 905 illustrates the reflection spectrum of the earth's surface in the time period of evening. As illustrated in graph 904, in the illumination spectrum in the time period of evening, the light intensity in the blue to the green regions is weakened in the time period of evening. Therefore, as illustrated in graph 905, the reflection spectrum has the light intensity smaller than it really is in the blue to green regions.

Thus, it is difficult to accurately calculate the vegetation index because the illumination spectrum from the sunlight changes according to the time period.

The illumination spectrum from the sunlight also changes according to the weather condition. Therefore, it is difficult to accurately calculate the vegetation index.

Hereinafter, an exemplary embodiment of the present disclosure will be described with reference to the accompanying drawings.

First Exemplary Embodiment

Figure 1:
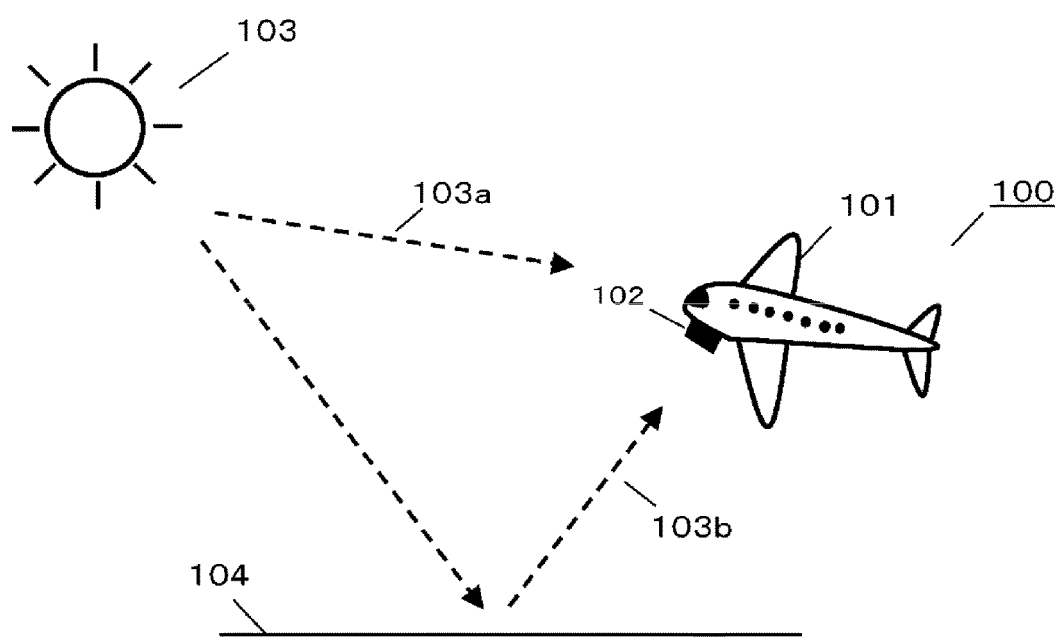
FIG. 1 is a conceptual diagram illustrating vegetation index calculation performed by a vegetation index calculation device according to a first exemplary embodiment.

FIG. 1 is a conceptual diagram illustrating the vegetation index calculation performed by vegetation index calculation device 100 according to a first exemplary embodiment. Vegetation index calculation device 100 includes flight vehicle 101, imaging unit 102 mounted on flight vehicle 101, and a controller (not illustrated). Vegetation index calculation device 100 acquires a spectrum (hereinafter, referred to as an illumination spectrum) of illumination light 103a with which earth's surface 104 is irradiated by light source 103 such as the sun using imaging unit 102, and acquires a spectrum (hereinafter, referred to as a reflection spectrum) of reflected light 103b reflected from earth's surface 104. Then, the controller calculates the vegetation index of earth's surface 104 using the illumination spectrum and the reflection spectrum.

Figure 2:
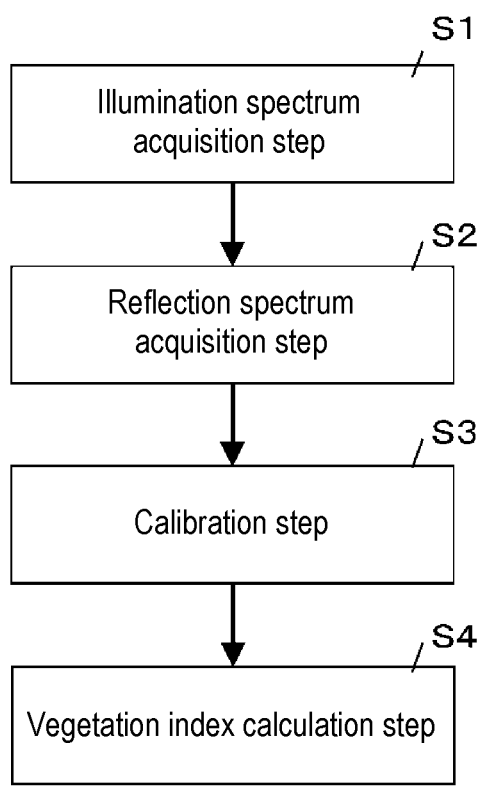
FIG. 2 is a flowchart illustrating the vegetation index calculation of the first exemplary embodiment.
Figure 3A:
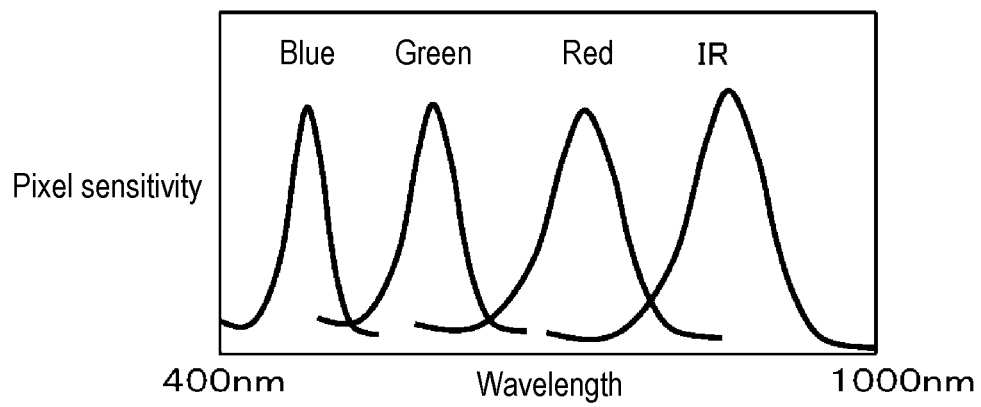
FIG. 3A is a spectrum diagram illustrating pixel sensitivity of an imaging unit of the first exemplary embodiment.
Figure 3B:
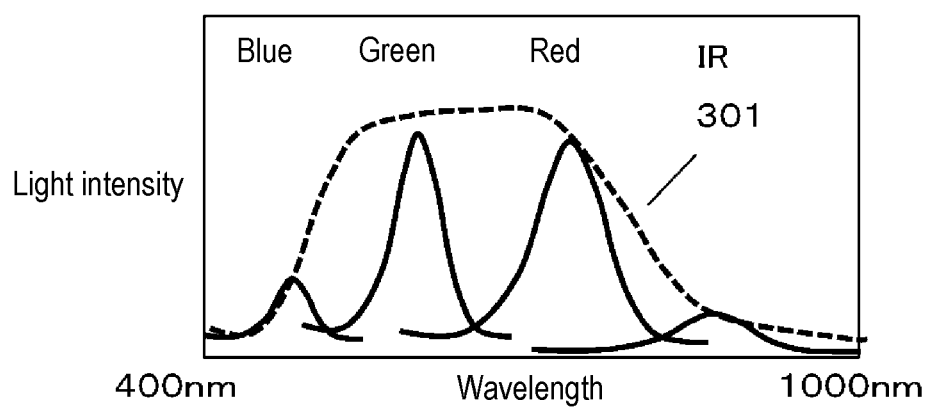
FIG. 3B is a diagram illustrating an illumination spectrum of sunlight in an earth's surface of the first exemplary embodiment.
Figure 3C:
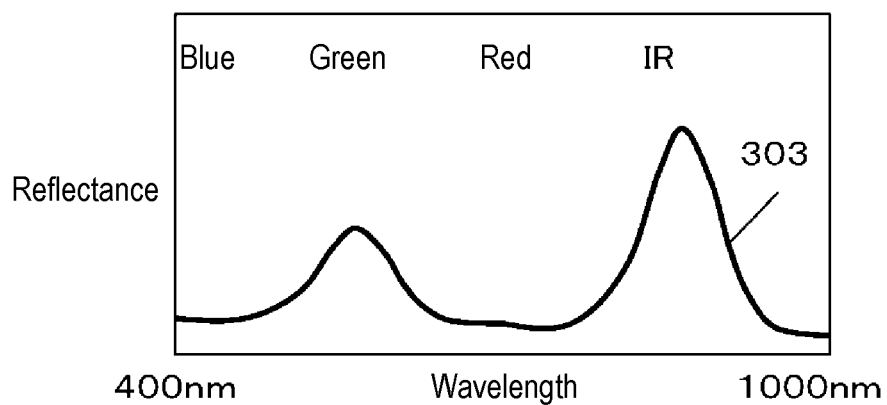
FIG. 3C is a spectrum diagram illustrating a reflectance of the earth's surface having a good vegetation state.
Figure 4:
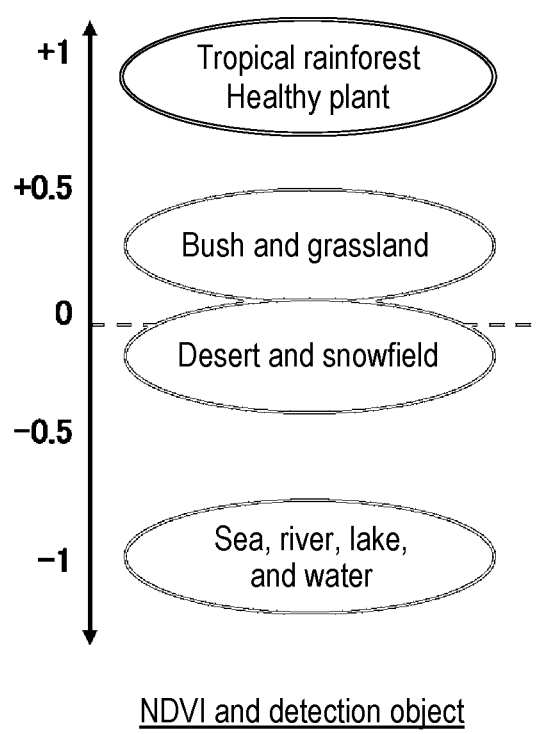
FIG. 4 is a diagram illustrating a relationship between a normalized difference vegetation index (NDVI) and a detection object.
Figure 5:
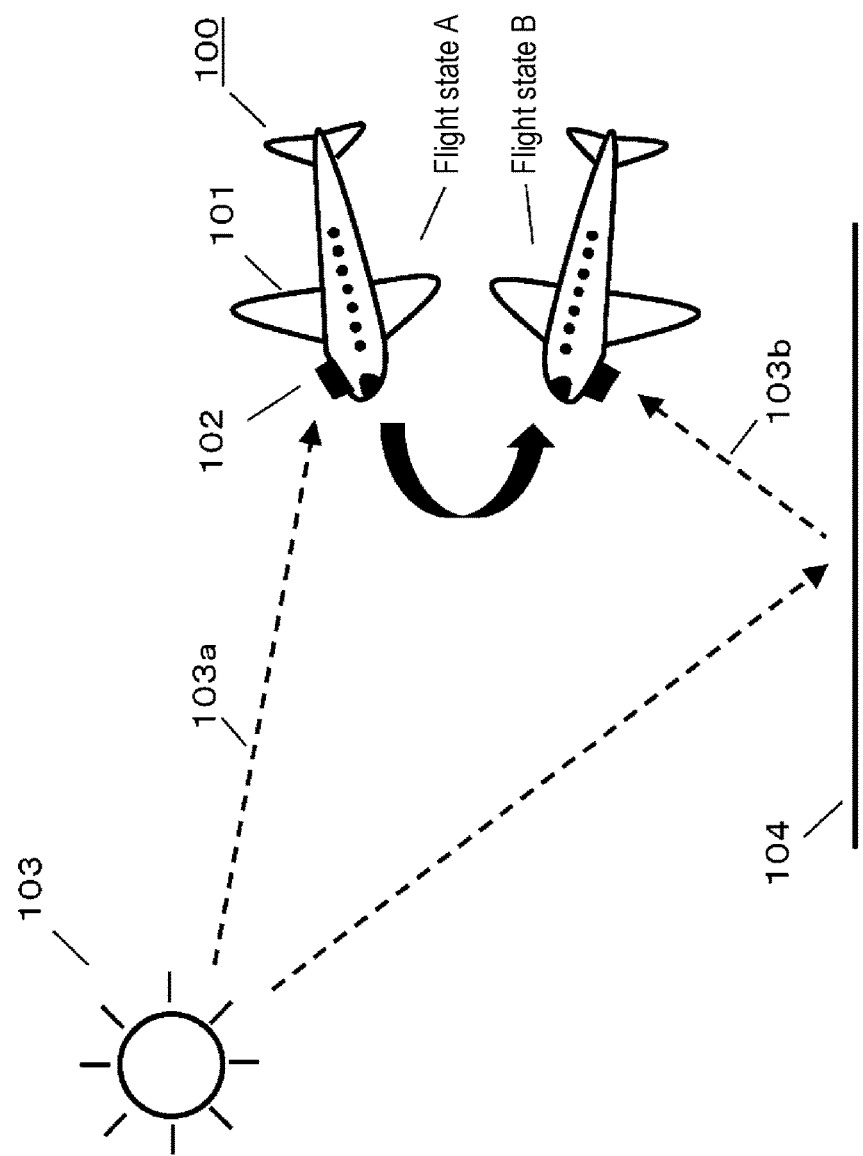
FIG. 5 is a view illustrating a spectrum capturing example performed by the vegetation index calculation device of the first exemplary embodiment.

A specific vegetation index calculation method of the first exemplary embodiment will be described with reference to FIGS. 2 to 4. FIG. 2 is a flowchart for calculating a vegetation index, FIGS. 3A to 3E are explanatory diagrams of a spectrum, FIG. 4 illustrates a relationship between a normalized difference vegetation index (NDVI) that is the vegetation index and a detection object, and FIG. 5 illustrates a spectrum capturing example performed by vegetation index calculation device 100.

Step S1 in FIG. 2 is an illumination spectrum acquisition step. In step S1, the spectrum of illumination light with which earth's surface 104 is irradiated by light source 103 is acquired using imaging unit 102. A camera that can acquire the spectrum from visible light to near-infrared light (about 400 nm to about 1000 nm) is used as imaging unit 102. FIG. 3A is a spectrum diagram illustrating pixel sensitivity of imaging unit 102 of the first exemplary embodiment. In FIG. 3A, a horizontal axis indicates the wavelength, and a vertical axis indicates the pixel intensity. Imaging unit 102 has substantially flat pixel intensity in the visible light to the near-infrared light. FIG. 3B is a diagram illustrating the illumination spectrum of the sunlight in earth's surface 104 of the first exemplary embodiment. In FIG. 3B, a horizontal axis indicates the wavelength, and a vertical axis indicates the light intensity. Illumination spectrum 301 (broken line) has the strong light intensity in the green and red regions, and has the weak light intensity in the blue and near-infrared regions. For this reason, similarly the intensity of the spectrum (solid line) acquired by imaging unit 102 is strong in the green and red regions, and is weak in the blue and near-infrared regions.

The illumination spectrum of the sunlight with which earth's surface 104 is irradiated is not a radiation spectrum of the sun that is light source 103, but the radiation spectrum is affected by reflection or absorption of dust or vapor in the air and gas such as ozone and carbon dioxide until the radiation spectrum reaches earth's surface 104 or vegetation index calculation device 100. The atmospheric state changes according to a climate or a weather (such as rain, cloudiness, and yellow sand). The spectrum of the illumination light with which earth's surface 104 or vegetation index calculation device 100 is actually irradiated is acquired in illumination spectrum acquisition step S1.

Step S2 in FIG. 2 is a reflection spectrum acquisition step. In step S2, the reflection spectrum reflected by earth's surface 104 is acquired using imaging unit 102. Generally, plants absorb wavelengths in blue and red regions, and strongly reflect a wavelength in a near-infrared region using chlorophyll included in a chloroplast. Therefore, as illustrated in FIG. 3C, reflectance 303 of the earth's surface having the good vegetation state is small in the blue and red regions, relatively large in the green region, and further large in the near-infrared region. Accordingly, when the illumination spectrum is flat, the reflection spectrum of a vegetation area is similar to the spectrum of reflectance 303. However, generally the illumination spectrum is uneven, and changes largely according to the weather condition or the time period. Particularly, when a small-scale aircraft in which a flight altitude is less than or equal to 1000 meters is used as flight vehicle 101, the small-scale aircraft is easily affected by the weather condition.

Figure 3D:
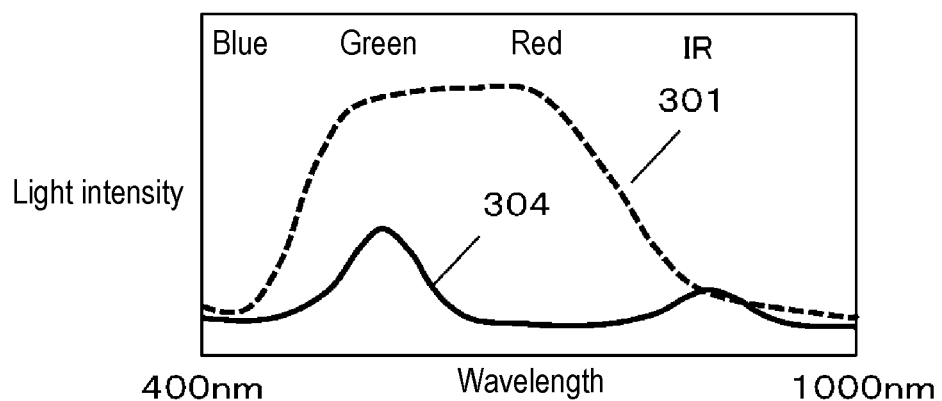
FIG. 3D is a diagram illustrating the illumination spectrum and a reflection spectrum, which are acquired by the imaging unit.

FIG. 3D illustrates illumination spectrum 301 and reflection spectrum 304, which are acquired by imaging unit 102. Reflectance 303 is large in the near-infrared region, and is suppressed by the influence of illumination spectrum in the near infrared region, thereby obtaining a spectral distribution of reflection spectrum 304.

Figure 3E:
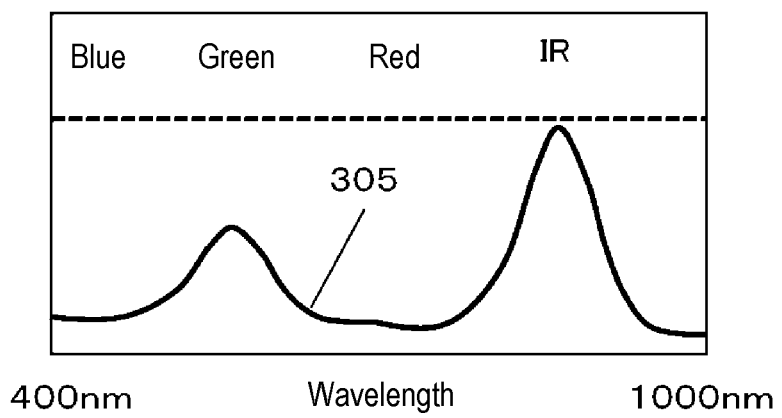
FIG. 3E is a diagram illustrating a calibrated spectrum in which an influence of the illumination spectrum is reduced with respect to a normalized reflection spectrum.

Step S3 in FIG. 2 is a calibration step. In step S3, reflection spectrum 304 is calibrated using illumination spectrum 301. As to a calibration method, for example, a signal output value of reflection spectrum 304 is divided by a signal output value of illumination spectrum 301 in each spectrum resolved into a predetermined range. Therefore, as illustrated in FIG. 3E, calibrated spectrum 305 in which the influence of illumination spectrum 301 is reduced can be obtained by normalizing reflection spectrum 304.

Step S4 in FIG. 2 is a vegetation index calculation step. In step S4, the vegetation index of earth's surface 104 is calculated based on calibrated spectrum 305. For example, the NDVI is used as the vegetation index. NDVI is an index indicating a distribution situation or an activity of the vegetation, and is defined by the following Mathematical Formula 1 using a character in which a healthy plant strongly reflects the near-infrared light near 700 nm. Where NIR is signal intensity in the near-infrared region, and Red is signal intensity in the red region.

$$NDVI = \frac{NIR - Red}{NIR + Red} \qquad \text{[Mathematical Formula 1]}$$

FIG. 4 is a diagram illustrating a relationship between the NDVI and the detection object. The NDVI becomes around +1 when the state of the earth's surface is a healthy plant of a tropical rainforest or the like, the NDVI becomes 0 to +0.5 when the state of the earth's surface is a bush or a grassland, the NDVI becomes −0.5 or more when the state of the earth's surface is a desert or a snowfield, and the NDVI becomes around −1 when the state of the earth's surface is a sea, a river, a lake, water, or the like. Although the NDVI standardly used as the vegetation index is described above, an enhanced NDVI in which the signal intensity in the green or blue region is used or another index has also been proposed. The vegetation index of the present invention is not limited to the NDVI, but any index in which the reflection spectrum of the earth's surface is used may be adopted as the vegetation index of the present invention.

FIG. 5 illustrates a spectrum capturing example performed by vegetation index calculation device 100. In illumination spectrum acquisition step S1, an air frame is turned over like flight state A under the control of flight vehicle 101, and the capturing is performed such that an image of at least a part of the sky is included in a capturing range of imaging unit 102. At this point, the capturing range of imaging unit 102 does not necessarily include an image of light source 103 such as the sun and an immediately upward direction directly facing the earth's surface, but the capturing range may include an image of a part of the sky that becomes a calibration reference. Because the acquired spectrum is deformed when the large light intensity exceeding a dynamic range of imaging unit 102 is input, desirably the capturing is performed such that an image of light source 103 is not included in the capturing range. Then, the air frame is returned like flight state B under the control of flight vehicle 101, and the capturing is performed while imaging unit 102 is oriented toward earth's surface 104 (the vegetation area that is an observation target). Thus, when the image of at least the part of the sky and an image of at least a part of earth's surface 104 are captured in two steps under the control of flight vehicle 101, both the illumination spectrum and the reflection spectrum can be acquired by one imaging unit. Therefore, cost reduction can be achieved compared with the case where a plurality of cameras are used, and an error caused by a difference in spectral characteristic between the plurality of cameras can be eliminated.

In the first exemplary embodiment, as illustrated in FIG. 2, reflection spectrum acquisition step S2 is performed after illumination spectrum acquisition step S1. Alternatively, reflection spectrum acquisition step S1 and illumination spectrum acquisition step S2 may be reversed. In the example of FIG. 5, the image of earth's surface 104 is captured first as flight state B, and then the image of light source 103 may be captured as flight state A.

Illumination spectrum acquisition step S1 and reflection spectrum acquisition step S2 are not necessarily performed as a series of operations. For example, the image of at least the part of the sky is captured to acquire the illumination spectrum by the first flight of flight vehicle 101, each image of each area of earth's surface 104 is captured by the second flight after flight vehicle 101 is landed once, and the reflection spectrum of each area may be acquired. Even in the one-time flight, the illumination spectrum is acquired only once, and the reflection spectrum from earth's surface 104 may be acquired a plurality of times in each area. Because a flight time is restricted to several tens of minutes in the small-scale aircraft in which a battery is used, desirably the spectrum is efficiently acquired in this way.

Although a satellite or an airplane can be used as the flight vehicle, the present invention is effective in a low-altitude flight vehicle, such as a helicopter and a drone, in which the flight altitude is less than or equal to 1000 meters, because the low-altitude flight vehicle is largely affected by a change in sunlight spectrum according to the weather condition or the time period.

In the first exemplary embodiment, the vegetation index calculation method and the vegetation index calculation device are described. However, the present disclosure is not limited to the vegetation, but can be applied to an index calculation of various states of the earth's surface such as a state grasp of an ocean, a lake, or a river, a state grasp of a desert or a snowfield, a situation grasp of a building, and a natural disaster situation grasp of an earth quake or a volcano. Even such index calculations include an illumination spectrum acquisition step of acquiring the illumination spectrum and a reflection spectrum acquisition step of acquiring the reflection spectrum of the earth's surface by the illumination light. The spectrum in which the influence of the illumination spectrum is reduced can be obtained through the calibration step of calibrating the reflection spectrum of the earth's surface using the illumination spectrum and the step of calculating the index of the state of the earth's surface based on the calibrated spectrum obtained in the calibration step, and the index of the state of the earth's surface can be calculated more accurately.

Second Exemplary Embodiment

A feature portion of an exemplary embodiment of a second exemplary embodiment will be described mainly with respect to points of difference from the first exemplary embodiment.

Figure 6:
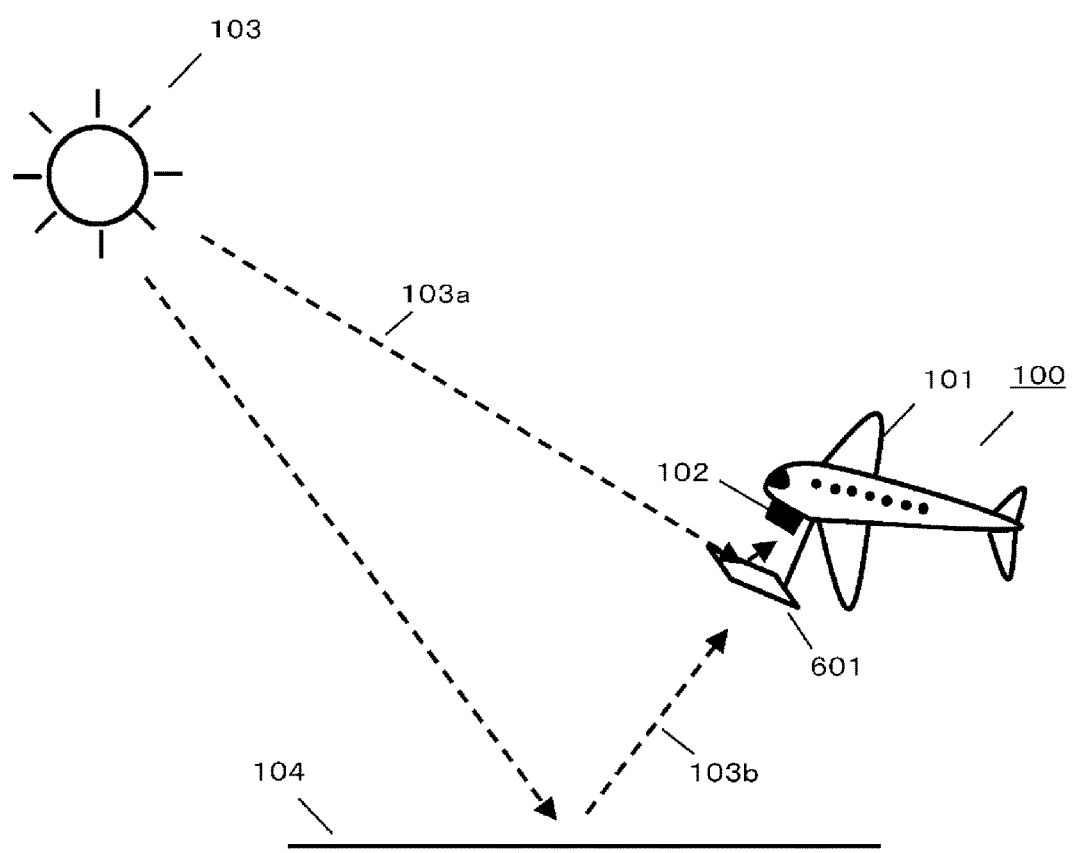
FIG. 6 is a view illustrating a spectrum capturing example performed by a vegetation index calculation device according to a second exemplary embodiment.

FIG. 6 illustrates another spectrum capturing example performed by vegetation index calculation device 100. Vegetation index calculation device 100 includes reflector 601 mounted on flight vehicle 101. Reflector 601 includes a movable mechanism.

In illumination spectrum acquisition step S1, a movable mechanism of reflector 601 moves reflector 601 between imaging unit 102 and earth's surface 104. At this point, illumination light 103a from light source 103 is adjusted so as to be reflected by reflector 601 to enter imaging unit 102. Then, imaging unit 102 captures an image of reflector 601. In reflection spectrum acquisition step S2, the movable mechanism of reflector 601 moves reflector 601 such that reflector 601 does not go between imaging unit 102 and earth's surface 104. Then imaging unit 102 captures an image of earth's surface 104.

Thus, when the light source and a subject (earth's surface) are captured in two steps using reflector 601, the illumination spectrum and the reflection spectrum can be acquired using one imaging unit without turning over the flight vehicle. Reflector 601 has the high reflectance in the range of 400 nm to 1000 nm, and desirably reflector 601 is made of a material having flat spectral characteristics or a material in which the spectral characteristics are already known.

The illumination spectrum is acquired using reflector 601 before a takeoff of flight vehicle 101, the image of each area of earth's surface 104 is captured after the takeoff, and the reflection spectrum of each area may be acquired. Even if the illumination spectrum and the reflection spectrum are acquired during the flight, the illumination spectrum is acquired only once, and the reflection spectrum may be acquired the plurality of times in each area. Because a flight time is restricted to several tens of minutes in the small-scale aircraft in which a battery is used, desirably the spectrum is efficiently acquired in this way.

Third Exemplary Embodiment

A feature portion of an exemplary embodiment of a third exemplary embodiment will be described mainly with respect to points of difference from the first exemplary embodiment.

Figure 7:
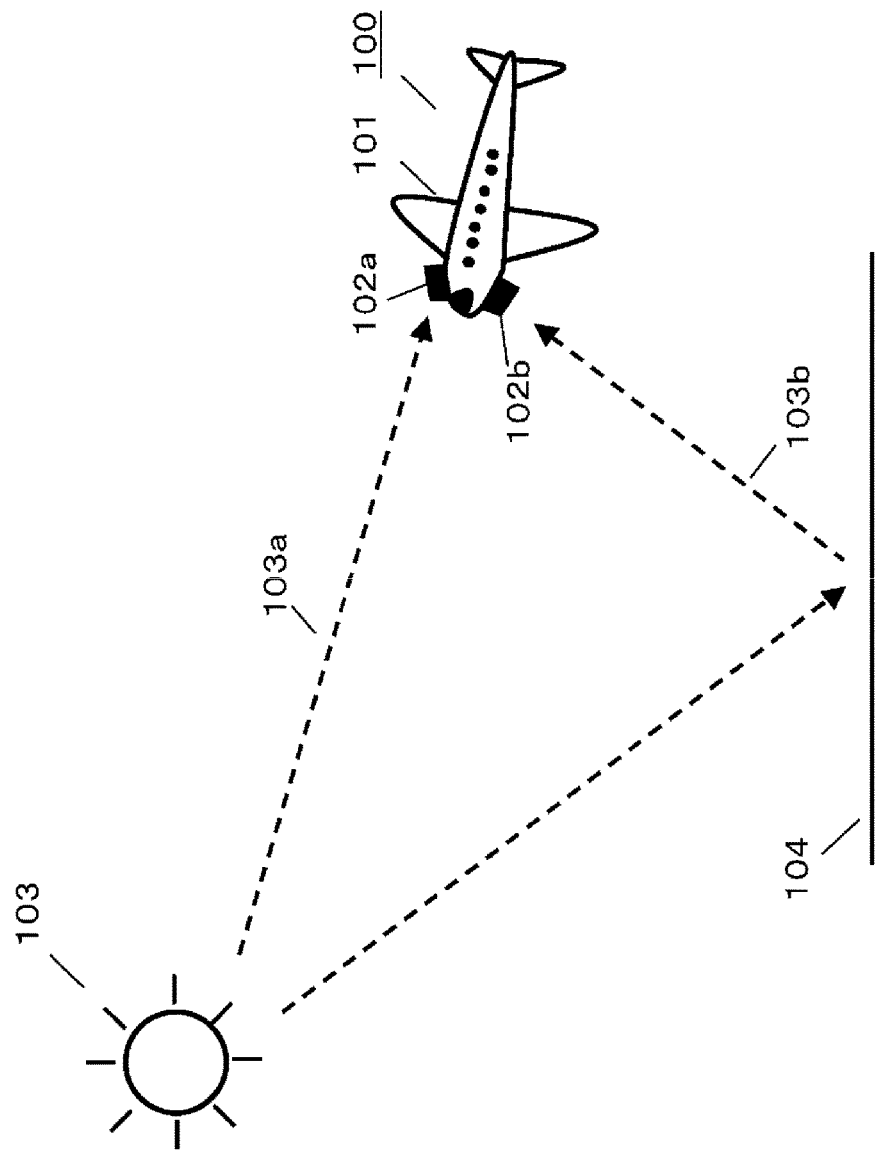
FIG. 7 is a view illustrating a spectrum capturing example performed by a vegetation index calculation device according to a third exemplary embodiment.
Figure 8:
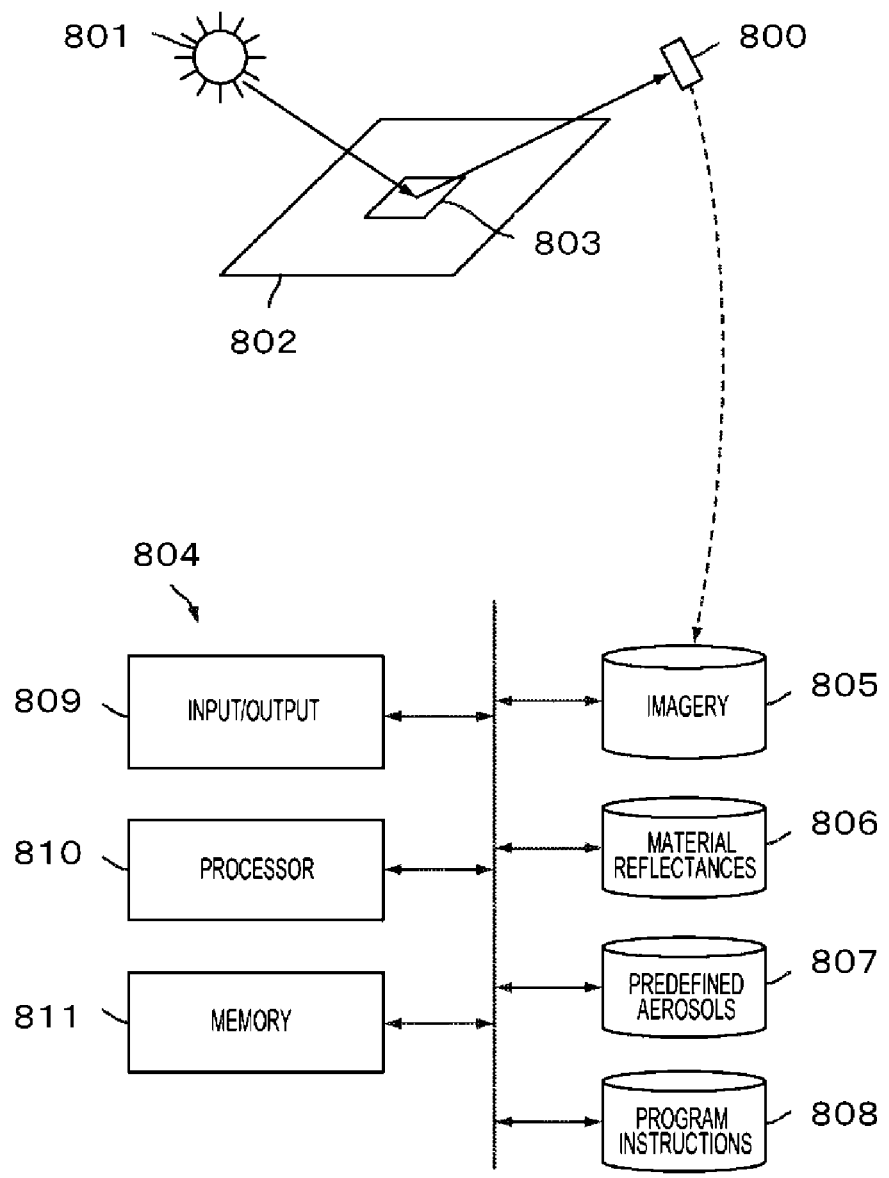
FIG. 8 is a diagram illustrating a conventional vegetation index calculation method and a conventional vegetation index calculation device.

FIG. 7 illustrates still another spectrum capturing example performed by vegetation index calculation device 100. In FIG. 7, imaging unit 102 is constructed with imaging unit 102a and imaging unit 102b. For example, imaging unit 102a is mounted on a place, such as a front portion or an upper portion of flight vehicle 101, where an image of the sky is easily captured. For example, imaging unit 102b is mounted on a place, such as a lower surface of flight vehicle 101, where the image of the earth's surface is easily captured.

In illumination spectrum acquisition step S1, the image of at least the part of the sky is captured using imaging unit 102a. In reflection spectrum acquisition step S2, the image of at least the part of earth's surface 104 is captured using imaging unit 1026b. At this point, step S1 and step S2 may sequentially or simultaneously be performed.

The capturing can be performed in a short time using two imaging units 102a, 102b without performing the turn-over operation of flight vehicle 101 or the control of reflector 601.

Resolution of imaging unit 102a may be set lower than resolution of imaging unit 102b. Because imaging unit 102a that captures an image of light source 103 is also used in the calibration, imaging unit 102a may have resolution lower than that of imaging unit 102b that captures the image of earth's surface 104 of an investigation target. Therefore, cost reduction of vegetation index calculation device 100 can be achieved.

Imaging unit 102a acquires the illumination spectrum only once, and imaging unit 102b may acquire the reflection spectrum the plurality of times in each area. Because a flight time is restricted to several tens of minutes in the small-scale aircraft in which a battery is used, desirably the spectrum is efficiently acquired in this way.

The vegetation index calculation method and vegetation index calculation device of the present disclosure can obtain the spectrum in which the influence of the illumination spectrum is reduced, and calculate the vegetation index more accurately, so that the vegetation index calculation method and vegetation index calculation device of the present disclosure are useful for the indexing of the vegetation state using a satellite or an unmanned aerial vehicle (UAV), for example.

The invention claimed is:

1. A vegetation index calculation method for calculating a vegetation index indicating a vegetation state in an earth's surface using a plurality of cameras and a flight vehicle, the vegetation index calculation method comprising:
   an illumination spectrum acquisition step of acquiring a spectrum of illumination light with which the earth's surface is irradiated;
   a reflection spectrum acquisition step of acquiring a reflection spectrum of the earth's surface by the illumination light;
   a calibration step of acquiring a calibrated spectrum by calibrating the reflection spectrum using the spectrum of illumination light; and
   a step of calculating the vegetation index of the earth's surface based on the calibrated spectrum obtained through the calibration step,
   wherein
   the plurality of cameras includes a first camera that is provided at a position where at least a part of sky can be captured and a second camera that is provided at a position where at least a part of the earth's surface can be captured,
   the illumination spectrum acquisition step includes acquiring the spectrum of the illumination light by capturing an image of at least the part of the sky using the first camera,
   the reflection spectrum acquisition step includes acquiring the reflection spectrum of the earth's surface by capturing an image of at least the part of the earth's surface using the second camera, and
   resolution of the first camera is set lower than resolution of the second camera.

2. The vegetation index calculation method according to claim 1, wherein the illumination spectrum acquisition step includes acquiring the spectrum of the illumination light by capturing an image of at least a part of sky using the first camera under control of the flight vehicle, and
   the reflection spectrum acquisition step includes acquiring the reflection spectrum of the earth's surface by capturing an image of at least a part of the earth's surface using the second camera under the control of the flight vehicle.

3. The vegetation index calculation method according to claim 1, wherein the flight vehicle includes a reflector that reflects the illumination light,
   the illumination spectrum acquisition step includes acquiring the spectrum of the illumination light by capturing the reflector using the first camera, and
   the reflection spectrum acquisition step includes acquiring the reflection spectrum of the earth's surface by capturing the earth's surface using the second camera.

4. The vegetation index calculation method according to claim 3, wherein the reflector includes a movable mechanism, and
   the illumination spectrum acquisition step includes moving the reflector between the first camera and the earth's surface before the first camera captures an image of the reflector.

5. The vegetation index calculation method according to claim 1, wherein the vegetation index is defined 'NDVI', the NDNI is defined by the following Mathematical Formula 1 using a character in which a healthy plant strongly reflects a near-infrared light near 700 nm, $$NDVI = \frac{NIR - \text{Red}}{NIR + \text{Red}} \qquad [\text{Mathematical Formula 1}]$$

where NIR is a signal intensity in a near-infrared region, and Red is a signal intensity in a red region.

6. The vegetation index calculation method according to claim 1, wherein in the calibration step, the spectrum of illumination light is multiplied by an reflection spectrum of plant.

7. A vegetation index calculation device that calculates a vegetation state in an earth's surface, the vegetation index calculation device comprising:
- a flight vehicle unit;
- a camera; and
- a controller,
- wherein the camera acquires a spectrum of illumination light and a reflection spectrum of the earth's surface by the illumination light,
- the controller calibrates the reflection spectrum using the spectrum of the illumination light to calculate a calibrated spectrum, and calculates a vegetation index in the earth's surface based on the calibrated spectrum,
- the camera acquires a spectrum of illumination light and a reflection spectrum of the earth's surface by the illumination light,
- the controller calibrates the reflection spectrum using the spectrum of the illumination light to calculate a calibrated spectrum, and calculates a vegetation index in the earth's surface based on the calibrated spectrum,
- the camera includes a first camera that is provided at a position where an image of at least a part of sky can be captured and a second camera that is provided at a position where an image of at least a part of the earth's surface can be captured,
- the spectrum of the illumination light is acquired using the first camera,
- the spectrum of the earth's surface is acquired using the second camera, and
- resolution of the first camera is set lower than resolution of the second imaging unit camera.

8. The vegetation index calculation device according to claim 7, wherein the flight vehicle unit performs flight control such that an image of at least a part of sky is included in a capturing range of the first camera when the first camera acquires the spectrum of the illumination light, and
- the flight vehicle unit performs flight control such that an image of at least a part of the earth's surface is included in the capturing range of the second camera when the second camera acquires the reflection spectrum of the earth's surface.

9. The vegetation index calculation device according to claim 7, further comprising a reflector that reflects the illumination light,
- wherein the first camera acquires the spectrum of the illumination light by capturing the image of the reflector.

10. The vegetation index calculation device according to claim 9, wherein the reflector includes a movable mechanism, and
- the reflector is moved between the first camera and the earth's surface before the first camera captures the image of the reflector.

11. The vegetation index calculation device according to claim 7, wherein the controller calibrates the reflection spectrum using the spectrum of the illumination light multiplied by an reflection spectrum of plant to calculate a calibrated spectrum.

* * * * *